United States Patent
Tseng et al.

(10) Patent No.: US 6,548,665 B2
(45) Date of Patent: Apr. 15, 2003

(54) ASYMMETRIC SYNTHESIS OF A KEY INTERMEDIATE FOR MAKING BENAZEPRIL AND ANALOGUES THEREOF

(75) Inventors: Wei-Hong Tseng, Kao-Hsiung (TW); George Schloemer, Longmont, CO (US)

(73) Assignee: Scinopharm, Taiwan, Ltd., Tainan (CN)

( * ) Notice: Subject to any disclaimer, the term of this patent is extended or adjusted under 35 U.S.C. 154(b) by 0 days.

(21) Appl. No.: 09/910,509

(22) Filed: Jul. 19, 2001

(65) Prior Publication Data

US 2002/0183515 A1 Dec. 5, 2002

Related U.S. Application Data

(60) Provisional application No. 60/291,888, filed on May 18, 2001.

(51) Int. Cl.$^7$ .............................................. C07D 223/16
(52) U.S. Cl. ...................................................... 540/523
(58) Field of Search ......................................... 540/523

(56) References Cited

PUBLICATIONS

Marianne Langston et al., "Racemisation of R–Bupivacaine: A Key Factor in the Integrated and Economic Process for the Production of Levobupivacaine", Organic Process Research & Development 2000, pp. 530–533.

Wen–chung Shieh, et al., "Asymmetric Synthesis of N–Substitutedx–Aminobenzlactam via Crystallization–Induced Asymmetric Transformation of Covalent Diastereomer", J. Org. Chem. 1997, 62, 8271–8272, pp. 8271–8272.

Von Stephen K. Boyer et al., "Note on the Synthesis of an Optically Active ACE Inhibitor with Amino–oxo–benzazepine–1–alkanoic–Acid Structure by Means of an Enantiocovergent Crystallization–Based Resolution", pp. 337–343. Helvicta Chimica Acta – vol. 71 (1998).

*Primary Examiner*—Bruck Kifle
(74) *Attorney, Agent, or Firm*—Cohen, Pontani, Lieberman & Pavane

(57) ABSTRACT

The present invention provides a method of converting an intermediate compound to the desired S,S diastereomer for efficiently making benazepril and analogues thereof.

7 Claims, 5 Drawing Sheets

FIG.3
RACEMISATION STUDY OF B4-ACID (ACIDIC CONDITION)

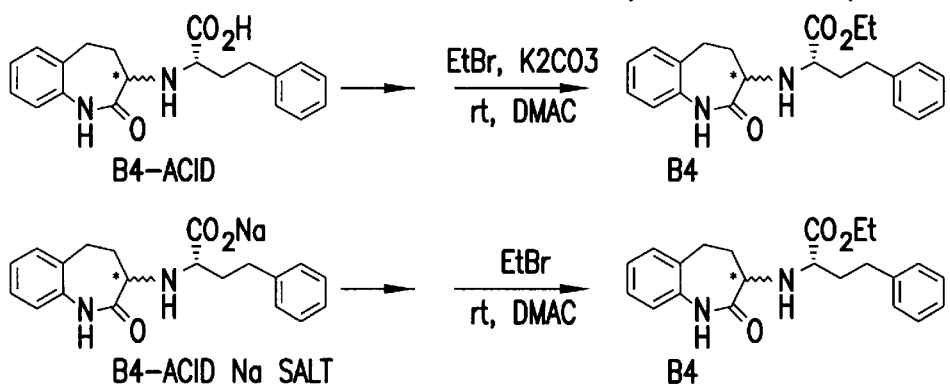

| BATCH No. | S.M. (23:77) | SOLVENT | TEMP. | TIME | D.P. RATIO (SS/RS) | O.P. RATIO (SS/RR) | NOTE |
|---|---|---|---|---|---|---|---|
| 0151-137 | B4-ACID | PROPIONIC ACID | 160°C (OUT) | 2h | >99:1 | 50:50 | |
| 0151-139 | B4-ACID | PROPIONIC ACID | 110°C (OUT) | 30 min | 98:2 | 70:30 | |
| 0151-139 | B4-ACID | PROPIONIC ACID | 110°C (OUT) | 60 min | 98:2 | 67:33 | |
| 0151-139 | B4-ACID | PROPIONIC ACID | 110°C (OUT) | 2h | >99:1 | 60:40 | |
| 0151-141 | B4-ACID | PROPIONIC ACID | rt | 30 min | 62:38 | 66:34 | SS:RR |
| 0151-141 | B4-ACID | PROPIONIC ACID | rt | 1h | 57:43 | 67:25:8[1] | SS:(RS+SR):RR |
| 0151-141 | B4-ACID | PROPIONIC ACID | 40°C | — | 70:30 | 90:10 | RS+SS:RR |
| 0151-141 | B4-ACID | PROPIONIC ACID | 60°C | — | 75:25 | 88:12 | RS+SS:RR |
| 0151-141 | B4-ACID | PROPIONIC ACID | 60°C | 30 min | 52:48 | 93:7 | RS+SS:RR |
| 0151-143 | B4-ACID | ACETIC ACID | rt | 30 min | 98:2 | 85:15 | |
| 0151-143 | B4-ACID | ACETIC ACID | rt | 60 min | 99:1 | 85:15 | |
| 0151-143 | B4-ACID | ACETIC ACID | rt | 2h | 99:1 | 86:14 | |
| 0151-145 | B4-ACID | PROPIONIC ACID P-XYLENE | rt | 30 min | 16:84 | 100 | |
| 0151-145 | B4-ACID | PROPIONIC ACID P-XYLENE | rt | 60 min | 47:53 | 93:7 | RS+SS:RR |
| 0151-145 | B4-ACID | PROPIONIC ACID P-XYLENE | rt | 2h | 25:75 | 97:3 | RS+SS:RR |

COSOLVENT SYSTEM STUDY OF B4-ACID OR B4-Na

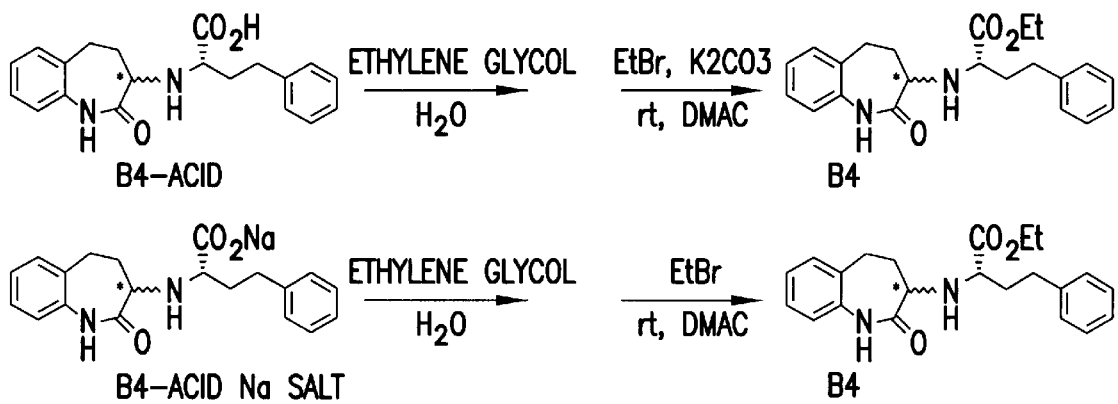

| BATCH No. | S.M. (23:77) | SOLVENT | TEMP. | TIME | D.P. RATIO (SS/RS) | O.P. RATIO (SS/RR) | NOTE |
|---|---|---|---|---|---|---|---|
| 0173-80 | B4-ACID | ETHYLENE-CLYCOL, H$_2$O | 160°C Δ | 8h | 98:2 | 86:14* | |
| 0173-82 | B4-ACID | ETHYLENE-CLYCOL, H$_2$O | 100°C Δ | 8h | 46:54 | 44:56* | |
| 0173-84 | B4-ACID | ETHYLENE-CLYCOL, H$_2$O | 138°C | 0.5h | 89:11 | 84:16* | |
| 0173-84 | B4-ACID | ETHYLENE-CLYCOL, H$_2$O | 138°C | 1h | 92:8 | 84:16* | |
| 0173-84 | B4-ACID | ETHYLENE-CLYCOL, H$_2$O | 138°C | 1.5h | 94:6 | 83:17* | |
| 0173-84 | B4-ACID | ETHYLENE-CLYCOL, H$_2$O | 138°C | 2.5h | 97:3 | 83:17* | |
| 0173-84 | B4-ACID | ETHYLENE-CLYCOL, H$_2$O | 138°C | 3.5h | 99:1 | 81:19* | |
| 0173-89 | B4-ACID | ETHYLENE-CLYCOL, H$_2$O | 115°C | 0.5h | 72:28 | 89:11* | |
| 0173-89 | B4-ACID | ETHYLENE-CLYCOL, H$_2$O | 115°C | 1h | 74:26 | 88:12* | |
| 0173-89 | B4-ACID | ETHYLENE-CLYCOL, H$_2$O | 115°C | 1.5h | 74:26 | 88:12* | |
| 0173-89 | B4-ACID | ETHYLENE-CLYCOL, H$_2$O | 115°C | 2h | 78:22 | 87:13* | |
| 0173-89 | B4-ACID | ETHYLENE-CLYCOL, H$_2$O | 115°C | 3h | 80:20 | 87:13* | |
| 0173-82 | B4-Na | ETHYLENE-CLYCOL, H$_2$O | 100°C Δ | 8h | 1:99 | 1:99* | |

RACEMISATION STUDY OF B4-ACID OR B4-Na

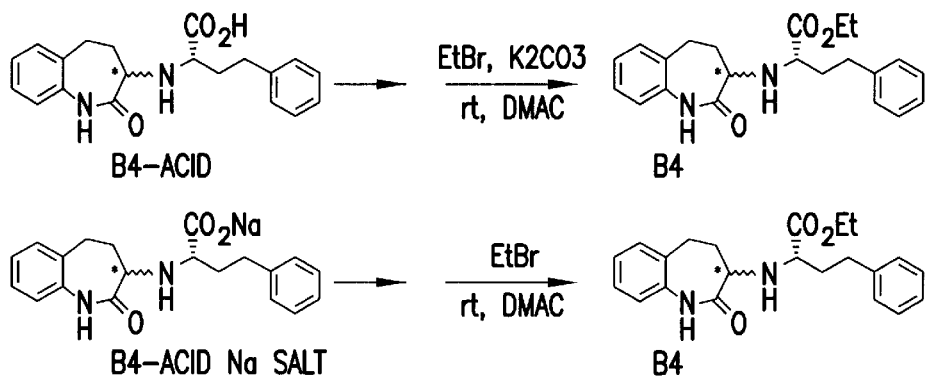

| BATCH No. | S.M. (23:77) | SOLVENT | TEMP. | TIME | D.P. RATIO (SS/RS) | O.P. RATIO (SS/RR) | NOTE |
|---|---|---|---|---|---|---|---|
| 0043-194-C | B4-ACID | P-XYLENE | 138°C | 48h | 98:02 | 86:14 | |
| 0308-001-B | B4-ACID | TOLUENE | 110°C | 16h | 22:78 | N/A | |
| 0308-005 | B4-ACID | P-XYLENE | 138°C | 4h | 92:8 | 87:13* | 95:5 |
| | B4-ACID | P-XYLENE | 138°C | 5.5h | 92:8 | N/A | |
| 0308-008 | B4-ACID | P-XYLENE | 138°C | 1h | 68:32 | N/A | |
| | | | | 2h | 81:19 | N/A | |
| | | | | 3h | 95:03 | 91:09* | 95:5 |
| 0043-186-A | B4-Na | P-XYLENE | 138°C | 16h | 40:60 | 45:55* | SOLVENT EVAPORATED |
| | B4-Na | P-XYLENE | 138°C | 32h | 50:50 | 56:44* | |
| 0043-194-D | B4-Na | P-XYLENE | 138°C | 48h | 03:97 | N/A | |
| 0308-004 | B4-Na | P-XYLENE | 138°C | 16h | 2:98 | N/A | |
| | B4-Na | P-XYLENE | 138°C | 24h | 1:99 | N/A | |
| 0043-186-B | B4-Na | P-XYLENE $K_2CO_3$ | 138°C | 16h | 30:70 | N/A | |
| | B4-Na | P-XYLENE $K_2CO_3$ | 138°C | 32h | 47:53 | 56:44* | |
| 0043-186-C | B4-Na | NET | 160°C | 16h | 36:64 | N/A | |
| 0308-001-A | B4-Na | TOLUENE | 110°C | 16h | 43:57* | N/A | TOLUENE EVAPORATED |
| | B4-Na | TOLUENE | 110°C | 32h | 39:61 | 41:59 | |

* (RS+SR+RR)

ASYMMETRIC SYNTHESIS OF A KEY INTERMEDIATE FOR MAKING BENAZEPRIL AND ANALOGUES THEREOF

This application claims the benefit of U.S. Provisional Application No. 60/291,888, filed May 18, 2001.

BACKGROUND OF THE INVENTION

1. Field of the Invention

The present invention relates to a method of asymmetric synthesis of a chemical compound. More particularly, the present invention relates to a method of converting a intermediate compound in synthesizing benazepril from one diastereomer form R,S (hereinafter the "RS" form) to another diastereomer form S,S (hereinafter the "SS" form), which is a desired form for making benazepril.

2. Description of the Related Art

It is generally known in the art that, for certain chemical compounds when used as therapeutic drugs, only one specific stereoisomer is effective. The other stereoisomers of the same compound may be less effective or have no effect at all. As a general technique, crystallization has been used to induce asymmetric synthesis, see Marianne Langston, et. al, *Organic Process Research & Development*, 4:530–533 (2000). The success of this method depends on a large solubility difference between the diastereomers and a condition that facilitates effective epimerization of the desired optical center. In a predetermined solvent, the desired diastereomer should have a low solubility and thus precipitates easily as crystals while the undesired diastereomer has a high solubility and thus largely remains in the solvent. As the more desired diastereomer forms crystals, its concentration in the solution becomes lower, a condition that helps further conversion from the undesired diastereomer to the desired one.

The synthesis of benazepril, an important angiotensin converting enzyme (ACE) inhibitor, is made difficult due to the need to prepare the SS form of the compound. The need to chemically resolve an early intermediate or to chemically synthesize a chiral intermediate adds much more expense to the synthesis. For example, Novartis Pharmaceuticals reported a method based on the crystallization technique, which converts one of the intermediate in the benazepril synthesis to the desired SS form. While this method produced a good yield of the desired SS chiral amide form, the necessary step of producing the homophenyl alanine portion is very expensive. In addition, the chiral S-phenylethyl amine used in the process is expensive and cannot be recovered, which further increases the costs. It would be much desired if (1) S-homophenyl alanine could be coupled with the benzlactam portion and (2) then induce chirality at the site alpha to the lactam. Our pending International Patent Application Serial Number PCT/1800/00478 disclosed a method of coupling between S-homophenyl alanine and benzlactam to accomplish the first step. To accomplish the second step in an efficient manner is one of the objects to be attained by the present invention.

BRIEF DESCRIPTION OF THE FIGURES

FIGS. 3–5 illustrate the results of epimerizing the mixture of diastereomers, either in their acid or salt forms, in the presence of various organic solvents, over a range of temperatures and time periods.

FIG. 3 illustrates the epimerization in the presence of propionic acid, acetic acid, and mixtures of propionic acid and p-xylene.

FIG. 4 illustrates the epimerization in the presence of mixtures of ethylene glycol and water.

FIG. 5 illustrates the epimerization in the presence of p-xylene alone, and followed with potassium carbonate in the presence of toluene.

SUMMARY OF THE INVENTION

This and other objects are accomplished by the present invention. Our pending International Patent Application Serial Number PCT/1800/00478 disclosed a method of producing compounds of the following formulae:

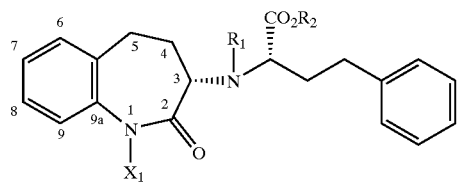

wherein $R_1$ is hydrogen, or a lower alkyl group having 1 to 4 carbon atoms;

$R_2$ is a lower alkyl group having 1 to 4 carbon atoms; and $X_1$ is a hydrogen.

The initial products obtained with the method disclosed therein is a mixture of two diastereomers (hereinafter "SS/RS")

Figure 1:
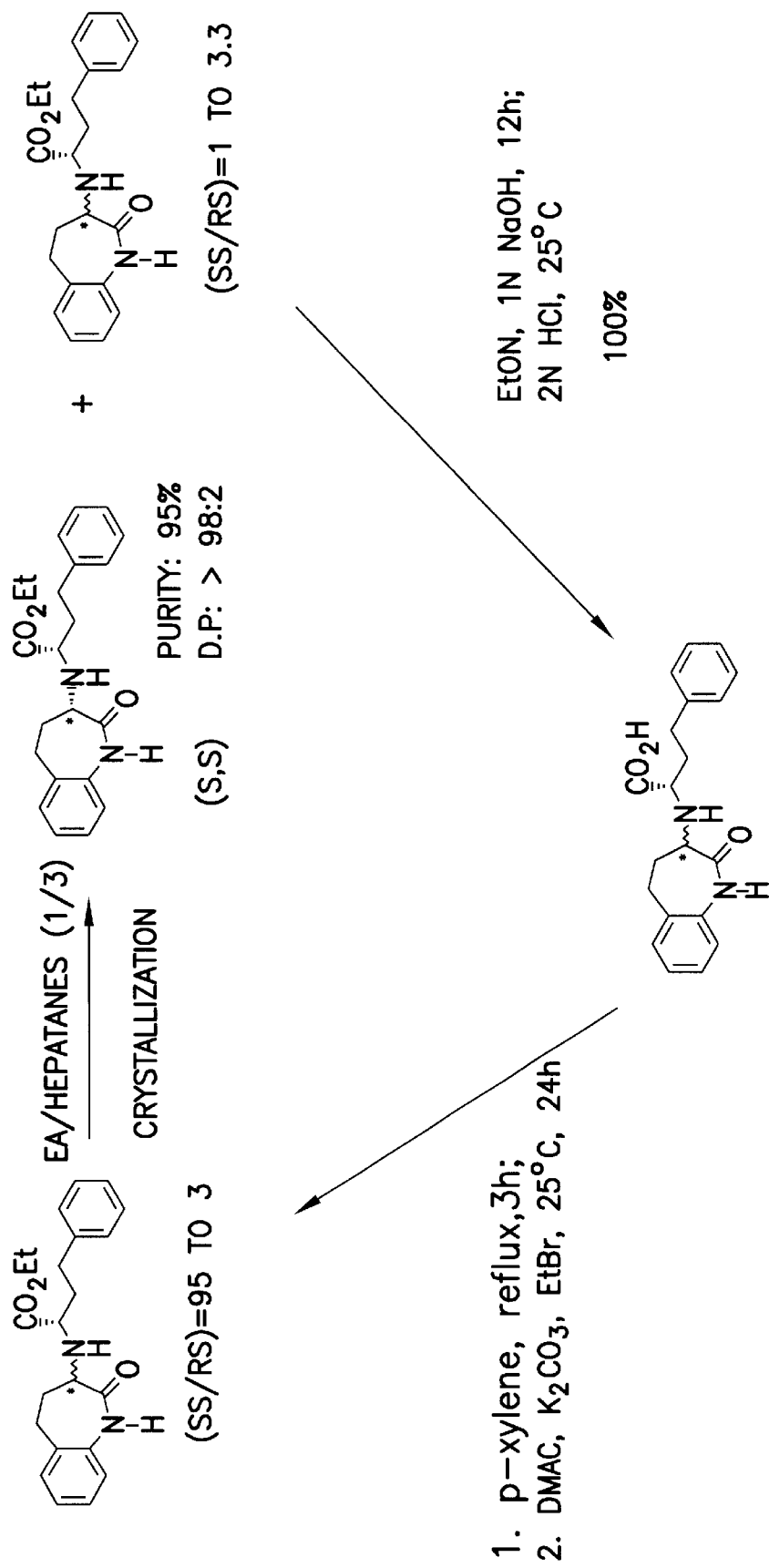
FIG. 1 schematically illustrates the present invention of recycling the mixture of two diastereomers through an epimerization step to increase the amount of the desired SS form.

By a conventional method, i.e., through simple crystallization, the desired SS form can be separated. However, the yield is approximately 30%. Thus, about 70% of the expensive material would be wasted. The present invention provides a recycling process to convert almost all the undesired RS form to the desired SS form as schematically illustrated in FIG. 1 and discussed below. The recycling process was complicated by the fact that the chiral position on the homophenyl alanine ester is more labile than the benzlactam chiral position under a variety of conversion conditions. Epimerization occurring on the wrong position would completely destroy the ability to recycle the material. The applicant discovered, however, that an initial conversion of the ester to a carboxylic acid could achieve two desired effects: (1) deactivating epimerization at the wrong position, i.e., the chiral position on the homophenyl alanine and (2) inducing reaction at the desired position, i.e., the benzlactam chiral position. The carboxylic acid compound, with a SS/RS ratio of about 1:3.3, subsequently undergoes a epimerization process, resulting in a predominantly SS diastereomer, up to a SS/RS ratio of 95:3. Once the carboxylic acid compound becomes predominantly the SS diastereomer, it is converted back to the ester compound, thereby completing the recycling process. The epimerization of the carboxylic acid compound takes place in two stages, first in p-xylene and reflux for 3 hours and then in DMAC, $K_2CO_3$ and EtBr at 25° C. for 24 hours. Under those conditions, not only is the desired position epimerized but the desired S chirality is induced selectively.

The above described epimerization and chiral induction can be achieved under a variety of conditions. The best results are obtained with the free acid, rather than the acid salts. The epimerization occurs thermally and therefore requires a sufficiently high temperature. The high temperature condition can be achieved by either using a high boiling-point solvent such as xylene or by heating the reaction mixture under pressure to increase its boiling-point temperature. Good results can be achieved in both polar and non-polar solvent systems, as long as the solubility and thermal requirements are met. For example, both p-xylene and ethylene glycol-water systems are found suitable to conduct the epimerization and chiral induction process. Propionic acid and acetic acid may also be used to conduct the epimerization and chiral induction process. The results of the epimerization or racemisation studies using various organic solvents are summarized in FIGS. 3 to 5.

The carboxylicacid compound can be converted back to the ester compound by re-esterification. The esterification can be carried out in a number of ways, for example, by reacting with ethyl bromide and potassium carbonate in dimethylacetamide.

The invention will be more specifically understood in terms of the following example, which is exemplary only and do not limit the scope of the invention.

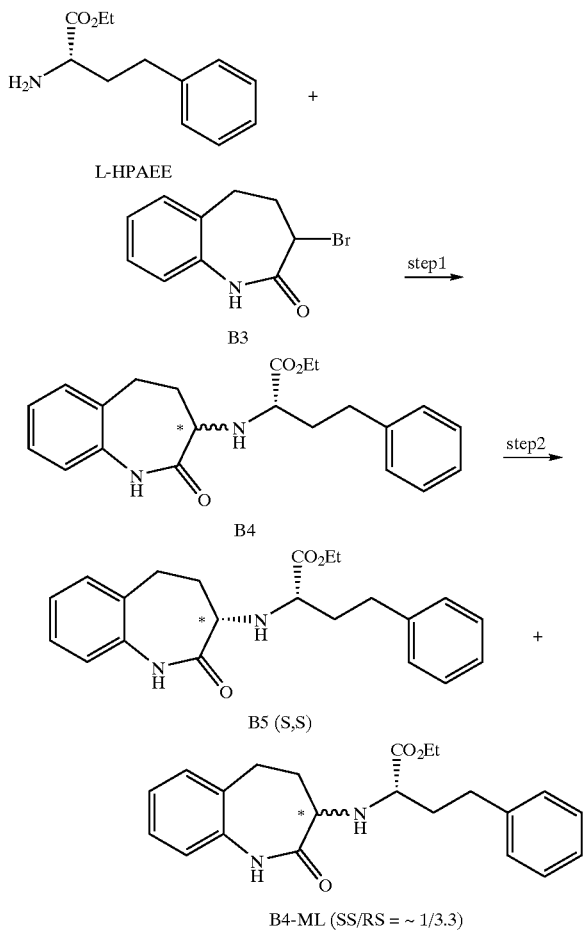

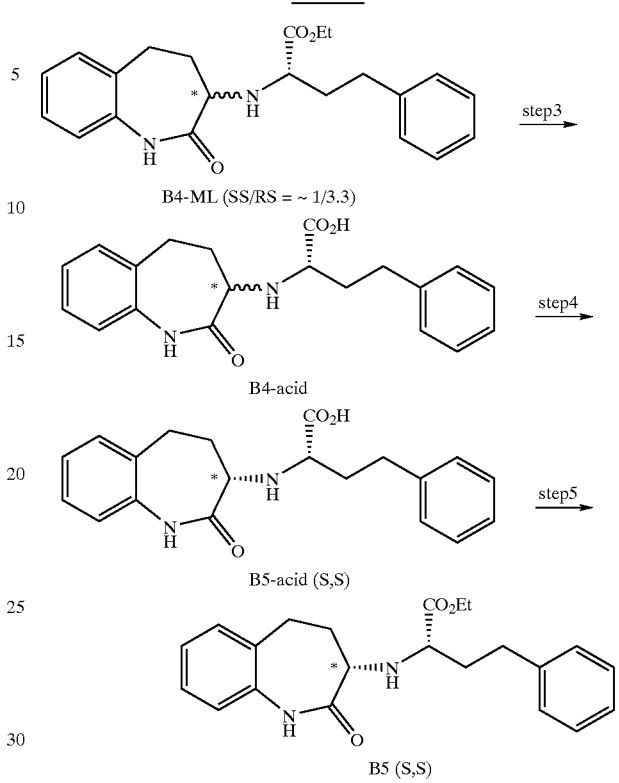

EXAMPLE I (1'S,3S)-3-[(1'-CARBONOXYL-3'-PHENYLPROPYL)AMINO]-2,3,4,5-TETRAHYDRO-2-OXO-1H-BENZAZEPINE B5-ACID (S,S)

B4 mother-liquid concentrate (550 g) obtained from the coupling reaction of 3-bromo-1,3,4,5-tetrahydro-2H-1-benzazepin-2-one (500 g) and L-HPAEE is dissolved in ethanol (1000 ml). 3N aqueous NaOH (2.4 L) is added to reaction mixture, then the mixture is stirred for 20 hours at room temperature. Subsequently a slurry is formed by adding 2 N hydrochloric acid (3436 ml). Liquid is removed to give a solid, which is dried at reduced pressure to give crude product B4-acid (450 g). p-Xylene (5 L) is added to B4-acid (450 g). The slurry is heated to reflux temperature for 30 h. The reaction mixture is cooled down to room temperature. Solvent removal results in a solid, which is then dried at reduced pressure to give 450 g of B5-acid (S,S) as a 98:2 diasteriomeric mixture as determined by HPLC, mp 287–290 C.; $^1$HNMR (DMSO, 400 MHz) 1.63–1.82(m, 2H), 1.88–2.04(m, 1H), 2.31–2.42(m, 1H), 2.50–2.80(m, 4H), 3.01 (t, J=6.2 Hz, 1H), 3.15(dd, J=7.8, 11.0 Hz, 1H), 4.02(br, 1H), 6.96(d, J=7.6 Hz, 1H), 7.08–7.16(m, 4H), 7.18–7.31(m, 4H), 9.88(s, 1H).

EXAMPLE II (1'S,3S)-3-[(1'-(ETHOXYCARBONYL)-3'-PHENYLPROPYL)AMINO]-2,3,4,5-TETRAHYDRO-2-OXO-1H-BENZAZEPINE B5 (S,S)

N,N-dimethylacetylamide (2 L), bromoethane (115 ml), and potassium carbonate (65 g) are added to the reaction mixture. The reaction is stirred for 48 hours. Then 3.5 L of water is added to the mixture at 10° C. The resulting precipitate is collected by filtration, washed with an additional 2 L of water, and dried at reduced pressure to give 520 g of crude solid. The resulting solid is dissolved in a mixture of 0.7 L of ethyl acetate and 2.8 L of n-Heptane at 80 C. The solution is cooled to 10 C. The product is isolated by filtration to obtain 230 g of B5 (S,S) as a >99:1 diasteriomeric mixture and as determined by HPLC, the ratio of enantiomers determined by HPLC is SS:RR>99:1. The overall yield is 30% from 3-bromo-1,3,4,5,-tetrahydro-2H-1-benzazepin-2-one; mp 119–120 C.; [ ]$_{20}$–204° (c=0.99, EtOH), IR(KBr): 3250 1726, 1671 cm$^{-1}$; 1HNMR (CDCl$_3$, 400 MHz) 1.14(t, J=7.2 Hz, 3H), 1.91–2.07(m, 3H), 2.43–2.53(m, 2H), 2.59–2.64(m, 2H), 2.68–2.75(m,2H), 2.82–2.92(m, 1H), 3.25–3.35(m, 2H), 4.01–4.11(m, 2H), 6.95–7.04(m, 1H), 7.10–7.29(m, 8H), 8.64–8.80(br s, 1H); $^{13}$CNMR (CDCl$_3$, 50 MHz) 14.1, 28.8, 32.0, 35.0, 37.8, 56.6, 60.0, 60.5, 122.0, 125.8, 125.9, 127.5, 128.2, 129.5, 134.3, 136.5, 141.3, 174.2, 175.2; HRMS, Cal. For $C_{22}H_{26}O_3N_2$: 366.1945(M+), found: 366.1950(M+)

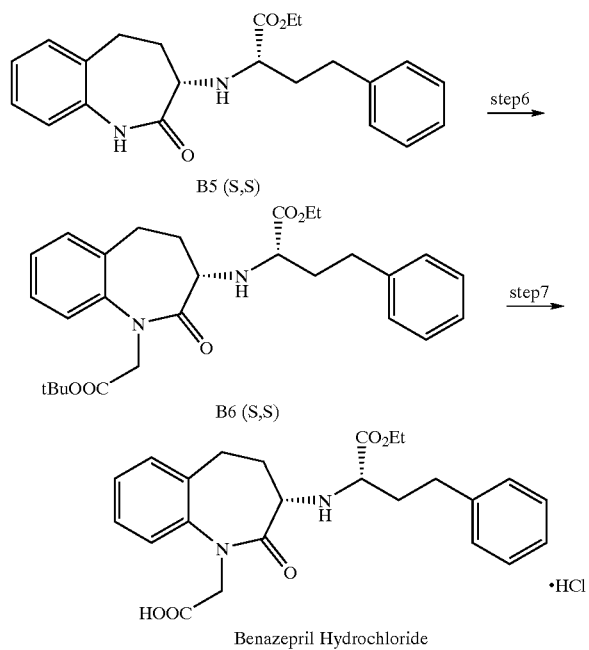

EXAMPLE III

3-[(1-(ETHOXYCARBONYL)-3-PHENYL-(1S)-PROPYL)AMINO]-2,3,4,5-TETRAHYDRO-2-OXO-1H[I]-10(3S)-BENZAZEPINE-1-ACETIC ACID MONOHYDROCHLORIDE SALT (BENAZEPRIL HYDROCHLORIDE)

Figure 2:
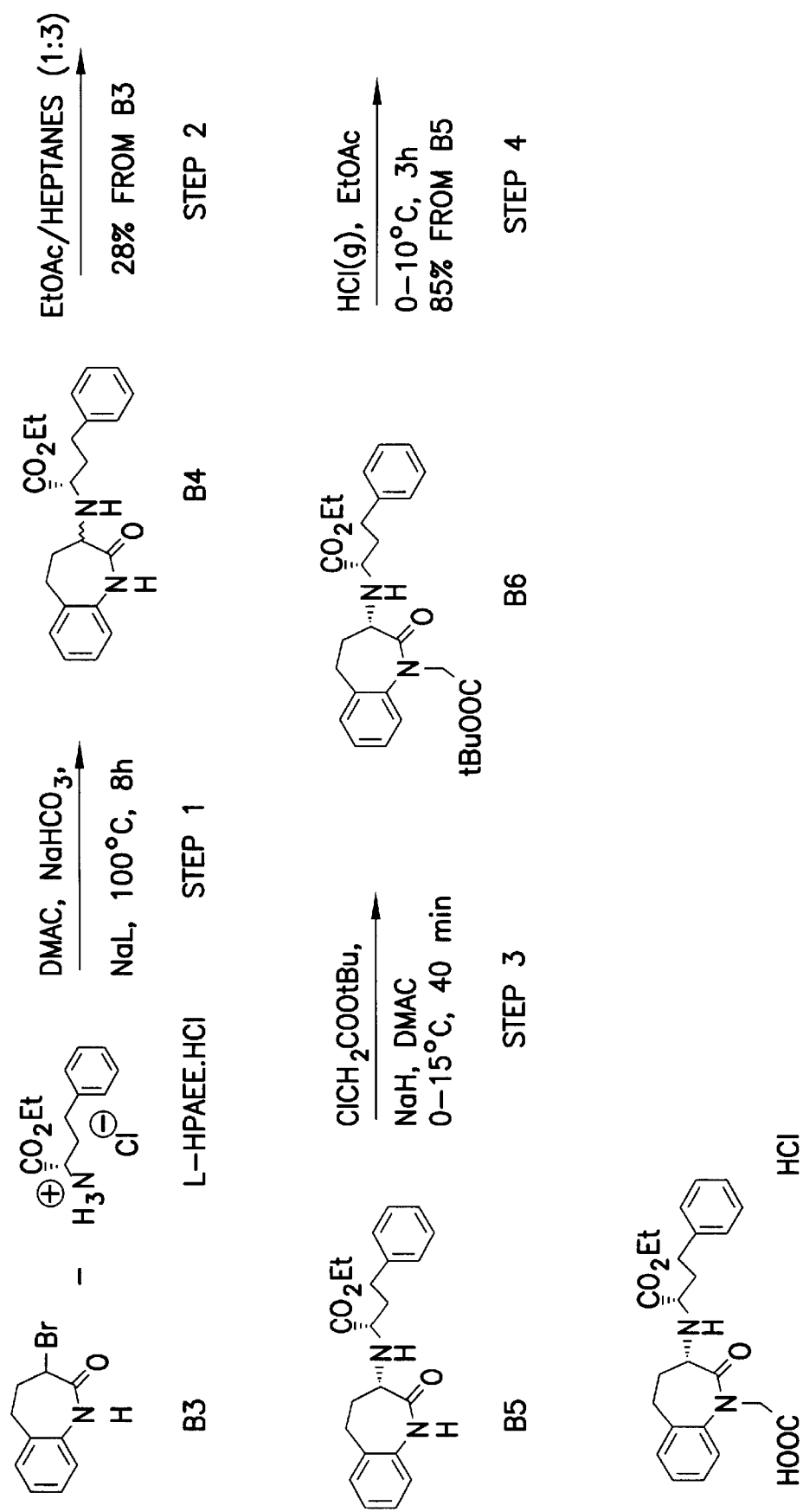
FIG. 2 illustrates the coupling of the S-homophenyl alanine with the benzlactam to produce the mixture of the two diastereomers, the epimerization step to increase the SS form, and the conversion of the SS form to benazepril hydrochloride.

The process steps and conditions of converting B5 to the final benazepril hydrochloride product is outlined in FIG. 2 and disclosed in detail in International Patent Application Serial Number PCT/1800/00478.

All references cited herein are hereby incorporated by reference.

We claim:

1. A process of epimerizing a carboxylic acid compound of formula II

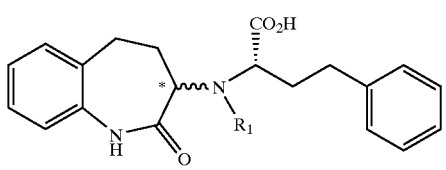

wherein $R_1$ is hydrogen, or a lower alkyl group having 1 to 4 carbon atoms, to increase the amount of the SS diastereomer of the compound of formula II by refluxing the carboxylic acid compound of formula II in a solution comprising an organic solvent.

2. The process of claim 1 wherein the SS diastereomer of the compound of formula II is covered by esterification to the ester compound of formula II

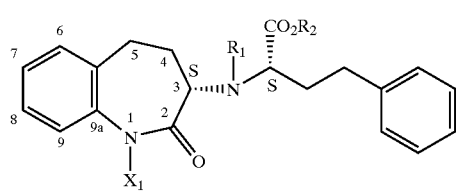

wherein $R_1$ is hydrogen, or a lower alkyl group having 1 to 4 carbon atoms;

$R_2$ is a lower alkyl group having 1 to 4 carbon atoms; and

X is a hydrogen, alkoxy carbonyl, or alkyl or alkylene having 1 to 4 carbon atoms.

3. The process of claim 2 wherein the SS diastereomer of the compound of formula II is converted to the ester compound of formula I by reacting the compound of formula II with an alkyl halide and potassium carbonate or potassium bicarbonate.

4. The process of claim 3 wherein the alkyl halide is ethyl bromide.

5. The process of claim 1 wherein the organic solvent is selected from the group consisting of p-xylene, xylenes, ethylene glycol, propionic acid and acetic acid.

6. The process of claim 5 wherein the process of epimerizing the carboxylic acid compound of formula II in p-xylene or xylenes further comprises the esterification of the compound of formula II by reacting the compound of formula II with n,n-dimethylacetylamide, bromoethane and potassium carbonate in said p-xylene or xylenes solution.

7. The process of claim 2 wherein the ester compound of formula I is benazepril.

* * * * *